US00PP24353P2

(12) United States Plant Patent
Sakazaki

(10) Patent No.: US PP24,353 P2
(45) Date of Patent: Mar. 25, 2014

(54) *CALIBRACHOA* PLANT NAMED 'USCAL5302M'

(50) Latin Name: ***Calibrachoa* sp.**
Varietal Denomination: USCAL5302M

(75) Inventor: Ushio Sakazaki, Shiga (JP)

(73) Assignee: Plant 21 LLC, Bonsall, CA (US)

( * ) Notice: Subject to any disclaimer, the term of this patent is extended or adjusted under 35 U.S.C. 154(b) by 53 days.

(21) Appl. No.: 13/507,518

(22) Filed: Jul. 5, 2012

(51) Int. Cl.
*A01H 5/00* (2006.01)

(52) U.S. Cl.
USPC ..... Plt./413

(58) Field of Classification Search
USPC ..... Plt./413
See application file for complete search history.

*Primary Examiner* — Annette Para
(74) *Attorney, Agent, or Firm* — C. A. Whealy

(57) ABSTRACT

A new and distinct cultivar of *Calibrachoa* plant named 'USCAL5302M', characterized by its upright, outwardly spreading to trailing and mounding plant habit; freely branching growth habit; dense and bushy appearance; early and freely flowering habit; dark yellow-colored flowers with a white-colored star pattern; and good garden performance.

1 Drawing Sheet

Botanical designation: *Calibrachoa* sp.
Cultivar denomination: 'USCAL5302M'.

BACKGROUND OF THE INVENTION

The present invention relates to a new and distinct cultivar of *Calibrachoa* plant, botanically known as *Calibrachoa* sp. and hereinafter referred to by the name 'USCAL5302M'.

The new *Calibrachoa* plant is a naturally-occurring branch mutation of a *Calibrachoa* sp. 'USCAL53002', disclosed in U.S. Plant Pat. No. 21,660. The new *Calibrachoa* plant was discovered and selected by the Inventor on a single flowering plant within a population of plants of 'USCAL53002' in a controlled greenhouse environment in Gensingen, Germany on Jun. 8, 2010. Asexual reproduction of the new *Calibrachoa* plant by terminal cuttings in a controlled environment in Gensingen, Germany since Jun. 8, 2010 has shown that the unique features of this new *Calibrachoa* plant are stable and reproduced true to type in successive generations.

SUMMARY OF THE INVENTION

Plants of the new *Calibrachoa* have not been observed under all possible environmental conditions and various cultural practices. The phenotype may vary somewhat with variations in environmental conditions such as temperature and light intensity without, however, any variance in genotype.

The following traits have been repeatedly observed and are determined to be the unique characteristics of 'USCAL5302M'. These characteristics in combination distinguish 'USCAL5302M' as a new and distinct *Calibrachoa* plant:

1. Upright, outwardly spreading to trailing and mounding plant habit.
2. Freely branching growth habit; dense and bushy appearance.
3. Early and freely flowering habit.
4. Dark yellow-colored flowers with a white-colored star pattern
5. Good garden performance. .

The new *Calibrachoa* plant can be compared to plants of the mutation parent, 'USCAL53002'. Plants of the new *Calibrachoa* differ primarily from plants of 'USCAL53002' in flower color as plants of 'USCAL53002' have solid dark yellow-colored flowers.

Plants of the new *Calibrachoa* can be compared to plants of the *Calibrachoa* 'USCALI402-1', disclosed in U.S. Plant Pat. No. 19,480. In side-by-side comparisons conducted in Bonsall, Calif., plants of the new *Calibrachoa* differed primarily from plants of 'USCALI402-1' in flower color as plants of 'USCALI402-1' had pale yellow-colored flowers.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant. The photograph at the bottom of the sheet comprises a side perspective view of a typical flowering plant of 'USCAL5302M' grown in a container. The photograph at the top of the sheet is a close-up view of a typical flowering plant of 'USCAL5302M'.

DETAILED BOTANICAL DESCRIPTION .

The aforementioned photographs and following observations, measurements and values describe plants grown during the spring in 11.4-cm containers in a polyethylene-covered greenhouse and finished in an outdoor nursery in Bonsall, Calif. During the production of the plants, day temperatures averaged 24° C. and night temperatures averaged 18° C. Plants were pinched one time and were seven weeks old when the photographs and description were taken. In the following description, color references are made to The Royal Horticultural Society Colour Chart, 2007 Edition, except where general terms of ordinary dictionary significance are used.

Botanical classification: *Calibrachoa* sp. 'USCAL5302M'.

Parentage: Naturally-occurring branch mutation of a *Calibrachoa* sp. 'USCAL53002', disclosed in U.S. Plant Pat. No. 21,660.

Propagation:

*Type*.—By terminal cuttings.

*Time to initiate roots, summer*.—About four days at temperatures ranging from 17° C. to 29° C.

*Time to initiate roots, winter*.—About six days at temperatures ranging from 17° C. to 21° C.

*Time to produce a rooted plant, summer*.—About 22 days at temperatures ranging from 17° C. to 29° C.

*Time to produce a rooted plant, winter*.—About 25 days at temperatures ranging from 17° C. to 21° C.

*Root description*.—Medium in thickness, fibrous; white in color.

*Rooting habit*.—Freely branching; medium density.

Plant description:

*Plant and growth habit*.—Upright, outwardly spreading to trailing and mounding plant habit; freely branching habit with about seven primary lateral branches each with about multiple secondary lateral branches; pinching enhances branching; moderately vigorous, dense and bushy growth habit.

*Plant height*.—About 12.5 cm.

*Plant diameter*.—About 26 cm by 30 cm.

Lateral branch description:

*Length*.—About 17.8 cm.

*Diameter*.—About 2 mm.

*Internode length*.—About 1.7 cm.

*Strength*.—Strong.

*Aspect*.—Initially upright to outwardly spreading to trailing.

*Texture*.—Pubescent.

*Color*.—Close to 146D tinted with close to 187B.

Foliage description:

*Arrangement*.—Before flowering, alternate; after flowering, mostly alternate to nearly opposite; leaves simple.

*Length*.—About 4.7 cm.

*Width*.—About 2 cm.

*Shape*.—Elliptical.

*Apex*.—Broadly acute.

*Base*.—Attenuate.

*Margin*.—Entire.

*Texture, upper and lower surfaces*.—Pubescent.

*Venation pattern*.—Pinnate; arcuate.

*Color*.—Developing leaves, upper surface: Close to 137A. Developing leaves, lower surface: Close to 146C. Fully expanded leaves, upper surface: Close to N137A; venation, close to 138A. Fully expanded leaves, lower surface: Close to 147B; venation, close to 138A.

*Petiole*.—Length: About 3 mm. Diameter: About 2 mm. Texture, upper and lower surfaces: Pubescent. Color, upper and lower surfaces: Close to 146D.

Flower description:

*Flower arrangement and habit*.—Single salverform flowers arising from leaf axils; freely flowering habit with usually about 42 open flowers and flower buds per lateral branch; flowers face upright to mostly outwardly.

*Fragrance*.—None detected.

*Natural flowering season*.—Early flowering habit, plants of the new *Calibrachoa* begin flowering about six weeks after planting; plants flower continuously from spring though the autumn in Southern California.

*Flower longevity*.—Individual flowers last about four to five days on the plant; flowers persistent.

*Flower diameter*.—About 3.7 cm.

*Flower length (height)*.—About 3.2 cm.

*Flower throat diameter*.—About 4 mm by 8 mm.

*Flower tube length*.—About 2 cm.

*Flower tube diameter, base*.—About 2.5 mm.

*Flower buds*.—Shape: Elongated oblong. Length: About 2.9 cm. Diameter: About 6 mm. Color: Close to 151D.

*Corolla*.—Arrangement: Five fused petals opening into a flared trumpet. Petal lobe length (from throat): About 1.4 cm. Petal lobe width: About 1.9 cm. Petal shape: Roughly obovate to spatulate. Petal apex: Rounded. Petal margin: Entire. Petal texture, upper surface: Smooth, glabrous. Petal texture, lower surface: Smooth, mostly glabrous with a few hairs along the veins. Throat texture: Smooth, glabrous. Tube texture: Pubescent. Color: Petal lobe, when opening, upper surface: Close to 7A; star pattern, close to NN155D. Petal lobe, when opening, lower surface: Close to 4C. Petal lobe, fully opened, upper surface: Close to 14B; star pattern, close to NN155D; venation, close to 145B; color does not fade with development. Petal lobe, fully opened, lower surface: Close to 8C; star pattern, close to NN155D; venation, close to 145A. Throat: Close to 7A; venation, close to 153A. Tube: Close to 4B; venation, close to 145A.

*Calyx*.—Arrangement: One star-shaped calyx tube with five sepals fused towards the base and arranged in a single whorl. Sepal length: About 1.4 cm. Sepal width: About 3 mm. Sepal shape: Lanceolate. Sepal apex: Acute. Sepal margin: Entire. Sepal texture, upper and lower surfaces: Pubescent. Color, upper surface: Close to 138A. Color, lower surface: Close to 138A to 138B.

*Peduncles*.—Length: About 2.2 cm. Diameter: About 1 mm. Angle: About 45° from stem axis. Strength: Strong. Texture: Pubescent. Color: Close to 146C.

*Reproductive organs*.—Stamens: Quantity: About five per flower. Filament length: About 1 cm. Filament color: Close to 145C. Anther shape: Oval. Anther length: About 1 mm. Anther color: Close to 12A. Pollen amount: Scarce. Pollen color: Close to 12C. Pistils: Quantity: One per flower. Pistil length: About 1 cm. Style length: About 8 mm. Style color: Close to 145C. Stigma shape: Round. Stigma color: Close to 146C. Ovary color: Close to 146D. Seeds and fruits: Seed and fruit development have not been observed on plants of the new *Calibrachoa*.

Garden performance: Plants of the new *Calibrachoa* have been observed to have good garden performance and tolerate wind, rain and temperatures ranging from about 1° C. to about 40° C.

Pathogen & pest resistance: Plants of the new *Calibrachoa* have not been observed to be resistant to pathogens and pests common to *Calibrachoa* plants.

It is claimed:

1. A new and distinct *Calibrachoa* plant named 'USCAL5302M' as illustrated and described.

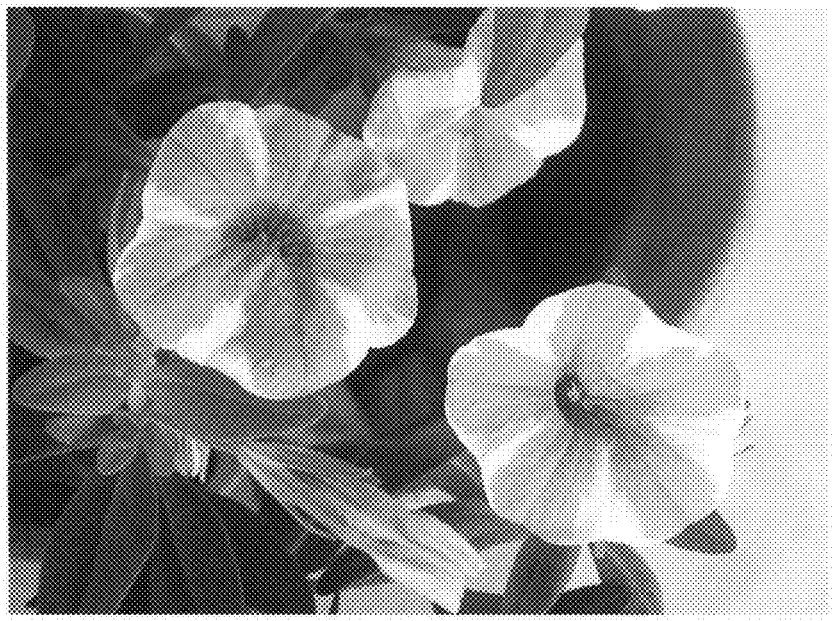
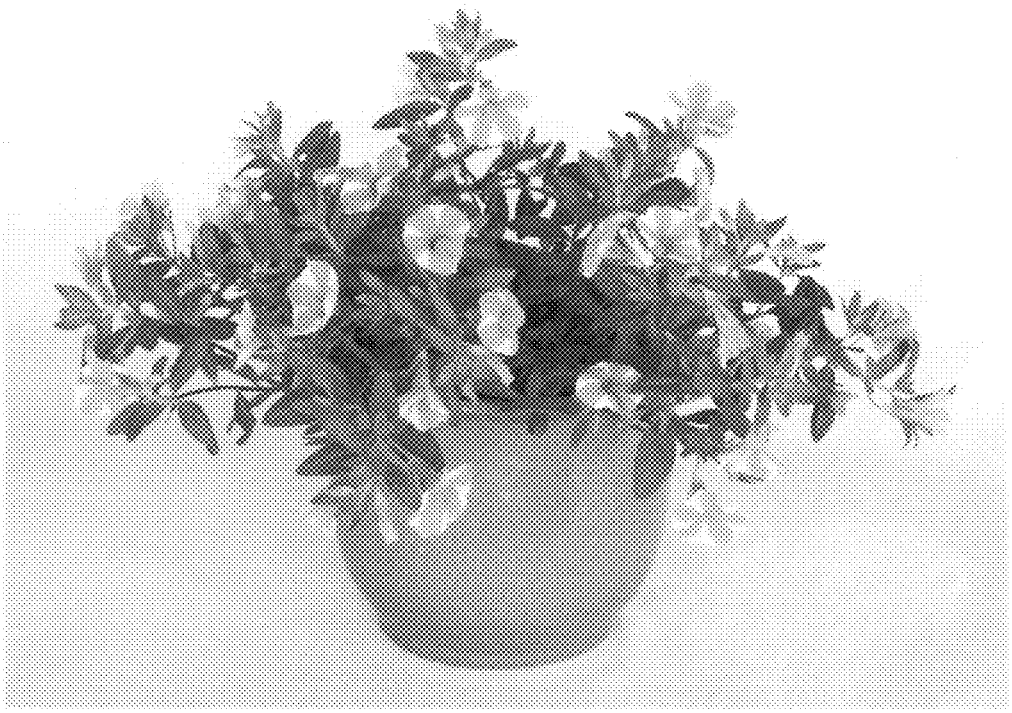

* * * * *